US012616449B2

(12) United States Patent
Gu et al.

(10) Patent No.: US 12,616,449 B2
(45) Date of Patent: May 5, 2026

(54) ULTRASONIC IMAGING SYSTEM, AND NON-TRANSITORY COMPUTER-READABLE MEDIUM

(71) Applicant: GE Precision Healthcare LLC, Waukesha, WI (US)

(72) Inventors: Minyu Gu, Wuxi (CN); Ke Tao, Wuxi (CN); Gang Liu, Wuxi (CN); Zhiwen Wang, Wuxi (CN); Shangjie Du, Wuxi (CN); Junjun Chen, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 62 days.

(21) Appl. No.: 18/536,083

(22) Filed: Dec. 11, 2023

(65) Prior Publication Data

US 2024/0206853 A1     Jun. 27, 2024

(30) Foreign Application Priority Data

Dec. 23, 2022    (CN) ......................... 202211664422.X

(51) Int. Cl.
  *A61B 8/08*        (2006.01)
  *A61B 8/00*        (2006.01)

(52) U.S. Cl.
  CPC .......... *A61B 8/5238* (2013.01); *A61B 8/4455* (2013.01); *A61B 8/4461* (2013.01); *A61B 8/4477* (2013.01); *A61B 8/463* (2013.01)

(58) Field of Classification Search
  CPC ... A61B 8/5238; A61B 8/4455; A61B 8/4461; A61B 8/4477; A61B 8/463; A61B 8/12; A61B 8/469; A61B 8/5246; A61B 8/5253; A61B 8/085
  See application file for complete search history.

(56) References Cited

U.S. PATENT DOCUMENTS

| | | | | |
|---|---|---|---|---|
| 5,377,682 | A | * 1/1995 | Ueno | A61B 8/445 600/585 |
| 2012/0203109 | A1* | 8/2012 | Tanabe | A61B 8/463 600/443 |
| 2016/0270757 | A1* | 9/2016 | Toma | A61B 8/5223 |
| 2022/0096797 | A1* | 3/2022 | Prince | A61B 8/469 |

FOREIGN PATENT DOCUMENTS

| | | |
|---|---|---|
| CN | 114271908 A | 4/2022 |
| CN | 113349897 B | 3/2023 |

* cited by examiner

*Primary Examiner* — Alexei Bykhovski

(57) ABSTRACT

An ultrasonic imaging method, including: during movement of a first ultrasonic transducer, receiving, over a period of time, an ultrasonic echo signal from tissue to be imaged; generating a first ultrasonic image set on the basis of the ultrasonic echo signals, the first ultrasonic image set including a plurality of ultrasonic images; identifying outer contours of a structure of interest in the plurality of ultrasonic images; and overlapping the outer contours of the structure of interest in the plurality of ultrasonic images to acquire a reconstructed image. Further provided in the present application are an ultrasonic imaging system and a non-transitory computer-readable medium.

14 Claims, 8 Drawing Sheets

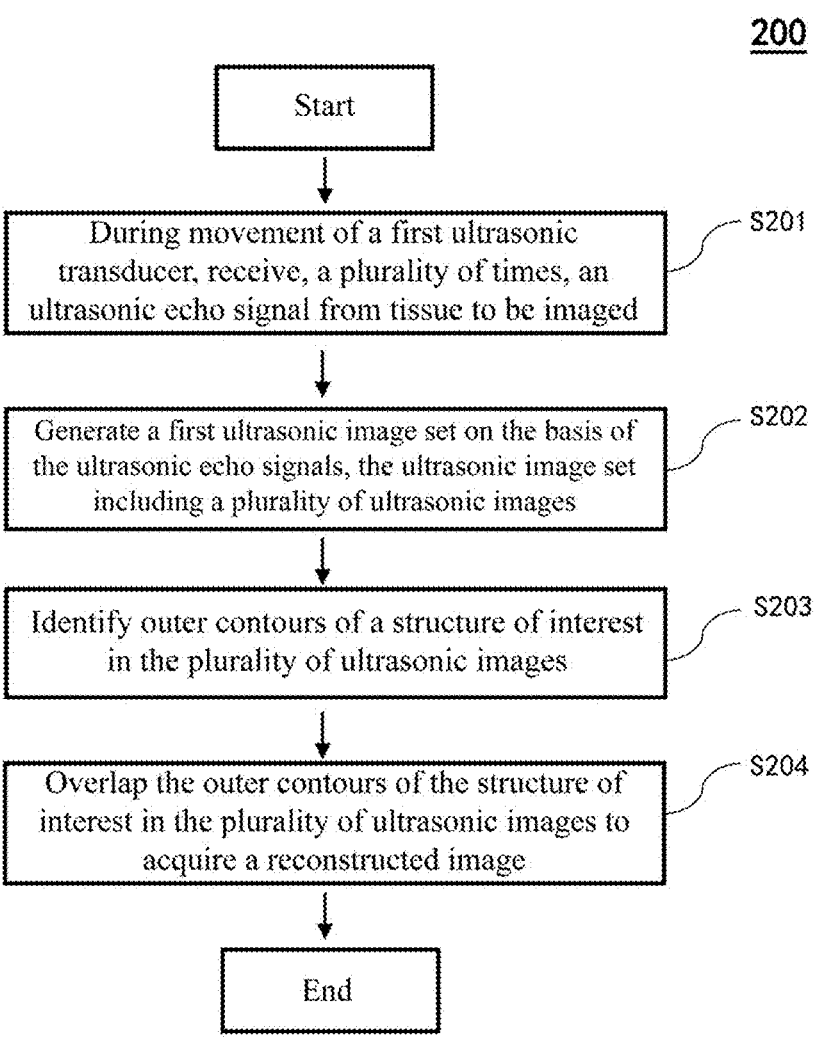

<u>200</u>

Start

During movement of a first ultrasonic transducer, receive, a plurality of times, an ultrasonic echo signal from tissue to be imaged — S201

Generate a first ultrasonic image set on the basis of the ultrasonic echo signals, the ultrasonic image set including a plurality of ultrasonic images — S202

Identify outer contours of a structure of interest in the plurality of ultrasonic images — S203

Overlap the outer contours of the structure of interest in the plurality of ultrasonic images to acquire a reconstructed image — S204

End

ULTRASONIC IMAGING SYSTEM, AND NON-TRANSITORY COMPUTER-READABLE MEDIUM

CROSS-REFERENCE TO RELATED APPLICATION

The present application claims priority to Chinese Patent Application No. 202211664422.X, filed on Dec. 23, 2022. The entire contents of the above-listed application are incorporated by reference herein in their entirety.

TECHNICAL FIELD

The present invention relates to the field of ultrasonic imaging and, in particular, to an ultrasonic imaging method, an ultrasonic imaging system, and a non-transitory computer-readable medium.

BACKGROUND

Ultrasonic imaging technology is a real-time, lossless imaging technology that utilizes a probe to receive an ultrasonic echo signal from a site to be imaged, and then processes the ultrasonic echo signal to perform imaging. In some application scenarios, ultrasonic imaging can assist determination of the position of a lesion in an interventional operation (e.g., a biopsy or treatment) in real time. For example, in an interventional operation on the prostate, a physician may use a probe running through a cavity (the rectum) to image the prostate and a lesion in the prostate in real time, so as to assist the physician in determining the position of the lesion, thereby performing sampling and/or treatment accurately.

The probe used in an interventional operation typically performs imaging to acquire a two-dimensional ultrasonic image. However, tissue to be imaged (e.g., the prostate) and a lesion therein have three-dimensional structures. In order to fully acquire the position and topology of a lesion, an operator needs to move the probe during imaging and performs manual observation, to determine the position of a sampling point or a treatment point. The outer contour of the lesion is typically irregular, so that repeated operation may be required during observation. Such a method relies to a great extent on the experience of an operator, and is time consuming.

SUMMARY

The aforementioned defects, deficiencies, and problems are solved herein, and these problems and solutions will be understood through reading and understanding the following description.

Provided in some embodiments of the present application is an ultrasonic imaging method, comprising: during movement of a first ultrasonic transducer, receiving, a plurality of times, an ultrasonic echo signal from tissue to be imaged; generating an ultrasonic image set on the basis of the ultrasonic echo signals, the ultrasonic image set comprising a plurality of ultrasonic images; identifying outer contours of a structure of interest in the plurality of ultrasonic images; and overlapping the outer contours of the structure of interest in the plurality of ultrasonic images to acquire a reconstructed image.

Provided in some embodiments of the present application is an ultrasonic imaging system, comprising: a probe, comprising a first ultrasonic transducer; a processor; and a display device, configured to receive a signal from the processor and perform a display operation. The processor is configured to perform the following method: during movement of a first ultrasonic transducer, receiving, a plurality of times, an ultrasonic echo signal from tissue to be imaged; generating an ultrasonic image set on the basis of the ultrasonic echo signals, the ultrasonic image set comprising a plurality of ultrasonic images; identifying outer contours of a structure of interest in the plurality of ultrasonic images; and overlapping the outer contours of the structure of interest in the plurality of ultrasonic images to acquire a reconstructed image.

Provided in some embodiments of the present application is a non-transitory computer-readable medium, the non-transitory computer-readable medium having a computer program stored thereon, the computer program having at least one code segment, and the at least one code segment being executable by a machine to perform the following method steps: during movement of a first ultrasonic transducer, receiving, a plurality of times, an ultrasonic echo signal from tissue to be imaged; generating an ultrasonic image set on the basis of the ultrasonic echo signals, the ultrasonic image set comprising a plurality of ultrasonic images; identifying outer contours of a structure of interest in the plurality of ultrasonic images; and overlapping the outer contours of the structure of interest in the plurality of ultrasonic images to acquire a reconstructed image.

It should be understood that the brief description above is provided to introduce, in a simplified form, concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any deficiencies raised above or in any section of the present disclosure.

BRIEF DESCRIPTION OF THE DRAWINGS

The present application will be better understood by reading the following description of non-limiting embodiments with reference to the accompanying drawings, wherein:

FIG. 2 is a schematic diagram of an ultrasonic imaging method according to some embodiments of the present application;

DETAILED DESCRIPTION

Specific implementations of the present invention will be described in the following. It should be noted that in the specific description of the implementations, it is impossible to describe all features of the actual implementations of the present invention in detail, for the sake of brief description. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless otherwise defined, the technical or scientific terms used in the claims and the description should be as they are usually understood by those possessing ordinary skill in the technical field to which they belong. "First", "second" and similar words used in the present invention and the claims do not denote any order, quantity or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
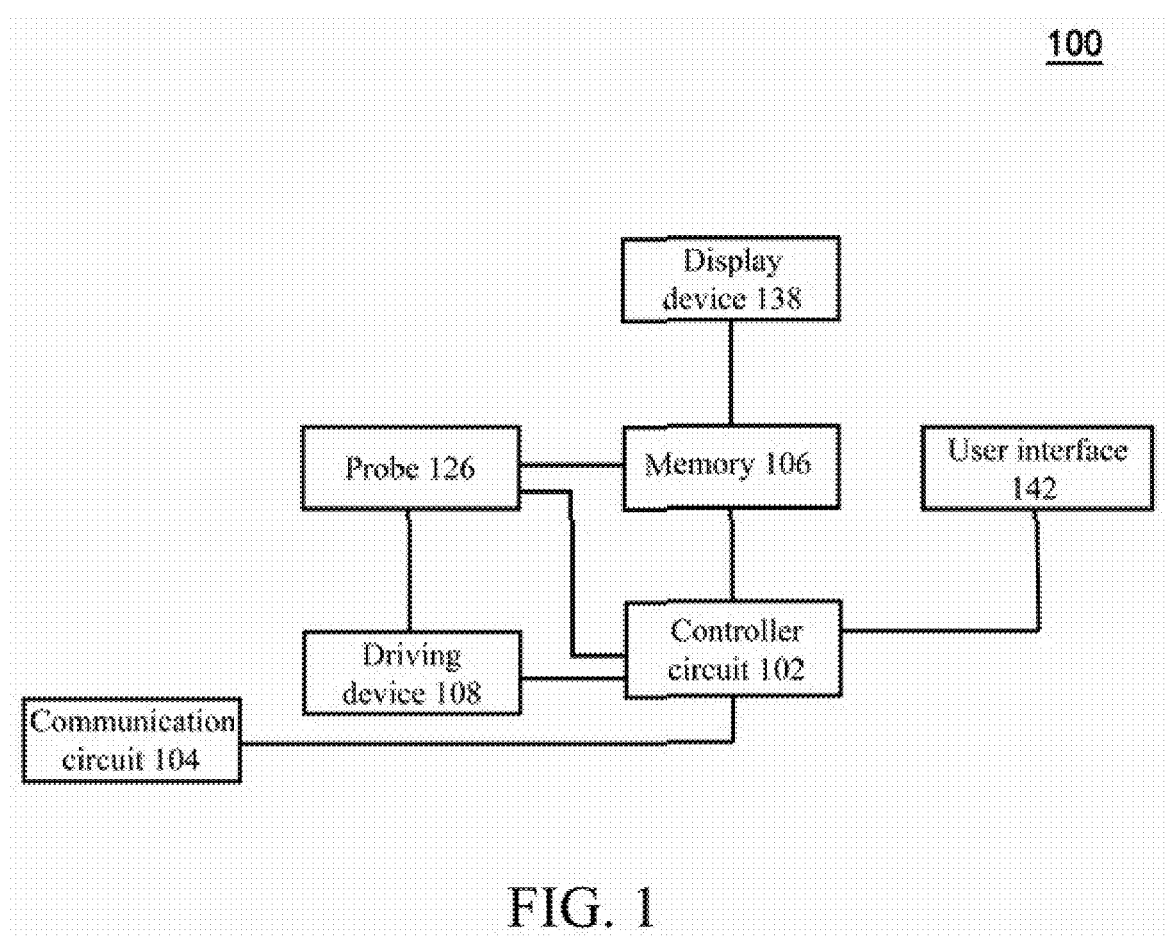
FIG. 1 is a schematic diagram of an ultrasonic imaging system according to some embodiments of the present application.

FIG. 1 shows a schematic block diagram of an embodiment of an ultrasonic imaging system 100. The ultrasonic imaging system 100 may include a controller circuit 102 operatively connected to a communication circuit 104, a display device 138, a user interface 142, a probe 126, a driving device 108, and a memory 106.

The controller circuit 102 is configured to control operation of the ultrasonic imaging system 100. The controller circuit 102 may include one or more processors. Optionally, the controller circuit 102 may include a central processing unit (CPU), one or more microprocessors, a graphics processing unit (GPU), or any other electronic assembly capable of processing inputted data according to a specific logic instruction. Optionally, the controller circuit 102 may include and/or represent one or more hardware circuits or circuitry, the hardware circuits or circuitry including, connecting, or including and connecting one or more processors, controllers, and/or other hardware logic-based devices. Additionally or alternatively, the controller circuit 102 may execute an instruction stored on a tangible and non-transitory computer-readable medium (e.g., the memory 106).

The controller circuit 102 may be operatively connected to and/or control the communication circuit 104. The communication circuit 104 is configured to receive and/or transmit information along a bidirectional communication link with one or more optional ultrasonic imaging systems, remote servers, etc. The remote server may represent and include patient information, a machine learning algorithm, a remotely stored medical image from a previous scan and/or diagnosis and treatment period of a patient, etc. The communication circuit 104 may represent hardware for transmitting and/or receiving data along a bidirectional communication link. The communication circuit 104 may include a transceiver, a receiver, a transceiver, etc., and associated circuitry (e.g., an antenna) for communicating (e.g., transmitting and/or receiving) in a wired and/or wireless manner with the one or more optional ultrasonic imaging systems, remote servers, etc. For example, protocol firmware for transmitting and/or receiving data along a bidirectional communication link may be stored in the memory 106 accessed by the controller circuit 102. The protocol firmware provides network protocol syntax to the controller circuit 102 so as to assemble a data packet, establish and/or segment data received along the bidirectional communication link, and so on.

The bidirectional communication link may be a wired (e.g., by means of a physical conductor) and/or wireless communication (e.g., utilizing radio frequency (RF)) link for exchanging data (e.g., a data packet) between the one or more optional ultrasonic imaging systems, remote servers, etc. The bidirectional communication link may be based on a standard communication protocol, such as Ethernet, TCP/IP, WiFi, 802.11, a customized communication protocol, Bluetooth, etc.

The controller circuit 102 is operatively connected to the display device 138 and the user interface 142. The display device 138 may include one or more liquid crystal display devices (e.g., light emitting diode (LED) backlights), organic light emitting diode (OLED) display devices, plasma display devices, CRT display devices, and the like. The display device 138 may display patient information, one or more medical images and/or videos, a graphical user interface, or a component received by the display device 138 from the controller circuit 102, one or more 2D, 3D or 4D ultrasonic image data sets from ultrasonic data stored in the memory 106, or anatomical measurement, diagnosis, processing information, and the like currently acquired in real time.

The user interface 142 controls the operation of the controller circuit 102 and the ultrasonic imaging system 100. The user interface 142 is configured to receive an input from a clinician and/or an operator of the ultrasonic imaging system 100. The user interface 142 may include a keyboard, a mouse, a trackball, a touch pad, one or more physical buttons, and the like. Optionally, the display device 138 may be a touch screen display device that includes at least a portion of the user interface 142. For example, a portion of the user interface 142 may correspond to a graphical user interface (GUI) that is generated by the controller circuit 102 and is shown on the display device 138. The touch screen display device may detect the presence of a touch from the operator on the display device 138, and may also identify the position of the touch relative to the surface area of the display device 138. For example, a user may select, by touching or contacting the display device 138, one or more user interface components of the user interface (GUI) shown on the display device. User interface components may correspond to icons, text boxes, menu bars, etc., shown on the display device 138. A clinician may select, control, and use a user interface assembly, interact with the same, and so on, so as to send an instruction to the controller circuit 102 to perform one or more operations described in the present application. For example, touch can be applied using at least one among a hand, a glove, a stylus, and the like.

The memory 106 includes a parameter, an algorithm, one or more ultrasonic examination protocols, data values, and the like used by the controller circuit 102 to perform one or more operations described in the present application. The memory 106 may be a tangible and non-transitory computer-readable medium such as a flash memory, a RAM, a ROM, an EEPROM, etc. The memory 106 may include a set of learning algorithms (e.g., a convolutional neural network algorithm, a deep learning algorithm, a decision tree learning algorithm, etc.) configured to define an image analysis algorithm. During execution of the image analysis algorithm, the controller circuit 102 is configured to identify a section (or a view or an anatomical plane) of an anatomical structure of interest in a medical image. Optionally, an image analysis algorithm may be received by means of the communication circuit 104 along one among bidirectional communication links, and stored in the memory 106.

The image analysis algorithm may be defined by one or more algorithms to identify a section of interest of a subject to be scanned of interest based on one or more anatomical features within the medical image (e.g., a boundary, thickness, pixel value change, valve, cavity, chamber, edge or inner layer, vessel structure, etc.), a modality or pattern of the medical image (e.g., color blood flow), etc. The one or more anatomical features may represent a feature of pixels and/or voxels of the medical image, such as a histogram of oriented gradients, a point feature, a covariance feature, a binary mode feature, and the like. For example, the image analysis algorithm may be defined by using prediction of object identification within the medical image by using one or more deep neural networks.

The image analysis algorithm may correspond to an artificial neural network formed by the controller circuit 102 and/or the remote server. The image analysis algorithm may be divided into two or more layers, such as an input layer for receiving an input image, an output layer for outputting an output image, and/or one or more intermediate layers. Layers of a neural network represent different groups or sets of artificial neurons, and may represent different functions that are executed by the controller circuit 102 with respect to an input image (e.g., an ultrasonic image acquired and/or generated by the ultrasonic imaging system 100) to identify an object of the input image and determine a section of an anatomical structure of interest shown in the input image. An artificial neuron in a layer of the neural network may examine an individual pixel in the input image. The artificial neurons use different weights in a function applied to the input image, so as to attempt to identify an object in the input image. The neural network produces an output image by assigning or associating different pixels in the output image with different anatomical features on the basis of the analysis of pixel characteristics.

The image analysis algorithm is defined by a plurality of training images, and the plurality of training images may be grouped into different anatomical planes of interest of the anatomical structure of interest. The training images may represent different orientations and/or cross sections of the anatomical structure of interest corresponding to different fields of view. Additionally or alternatively, the image analysis algorithm may be defined by the controller circuit on the basis of a classification model. The classification model may correspond to a machine learning algorithm based on a classifier (e.g., a random forest classifier, principal component analysis, etc.) configured to identify and/or assign anatomical features to multiple types or categories based on overall shape, spatial position relative to the anatomical structure of interest, intensity, etc.

The controller circuit 102 executing an image analysis algorithm (e.g., an image analysis algorithm) may determine a section corresponding to a current ultrasonic image based on the relationship of the anatomical features relative to each other, modality, etc.

Additionally or alternatively, the controller circuit 102 may define a separate image analysis algorithm customized and/or configured for different selected anatomical structures of interest. For example, multiple image analysis algorithms may be stored in the memory 106. Each algorithm among the plurality of image analysis algorithms may be customized and/or configured on the basis of different training images (e.g., a set of input images) to configure layers of different neural networks, so as to select anatomical structures of interest, classification models, supervised learning models, and the like.

With continued reference to FIG. 1, the ultrasonic imaging system 100 may include a probe 126 and a driving device 108. The driving device 108 is connected to the probe 126 and the controller circuit 102 to receive a control signal of the controller circuit 102 to drive, under the control thereof, the probe 126 to move. The driving device 108 includes a motor and an action mechanism connected to the motor. In an example, the action mechanism driven by the motor can drive the probe to move. Motion forms may include rectilinear motion, rotation, etc., thereby satisfying different scan requirements. In an interventional operation, the driving device 108 drives the probe 126 to move rectilinearly, thereby adjusting the depth of the probe 126 in the body of a person to be imaged. The driving device 108 may also drive the probe 126 to rotate. Combination of rectilinear motion and rotation enables the probe 126 to image tissue to be imaged in different directions, thereby satisfying different scan requirements.

The probe 126 has elements such as an ultrasonic transducer, a transmitter, a transmission beamformer, a detector/SAP electronics, etc., (not shown). The detector/SAP electronics may be used to control switching of transducer elements. The detector/SAP electronics may also be used to group the transducer elements into one or more sub-holes. Configurations of the probe 126 will also be described below exemplarily.

The probe 126 may be configured to acquire ultrasonic data or information from an anatomical structure of interest (e.g., organs, blood vessels, heart, bones, etc.) of a patient. The probe 126 is communicatively connected to the controller circuit by means of the transmitter. The transmitter transmits a signal to the transmission beamformer on the basis of acquisition settings received by the controller circuit 102. The acquisition settings may define the amplitude, pulse width, frequency, gain setting, scanning angle, power, time gain compensation (TGC), resolution, and the like of ultrasonic pulses emitted by the ultrasonic transducer. The ultrasonic transducer emits a pulsed ultrasonic signal into a patient (e.g., the body). The acquisition settings may be defined by a user operating the user interface 142. The signal transmitted by the transmitter, in turn, drives the ultrasonic transducer.

The ultrasonic transducer transmits a pulsed ultrasonic signal to a body (e.g., a patient) or a volume that corresponds to an acquisition setting along one or more scanning planes. The ultrasonic signal may include, for example, one or more reference pulses, one or more push pulses (e.g., shear waves), and/or one or more pulsed wave Doppler pulses. At least a portion of the pulsed ultrasonic signal is backscattered from the tissue to be imaged (e.g., the organ, bone, heart, breast tissue, liver tissue, cardiac tissue, prostate tissue, newborn brain, embryo, abdomen, etc.) to produce an echo. Depending on the depth or movement, the echo is delayed in time and/or frequency, and received by the ultrasonic transducer. The ultrasonic signal may be used for imaging, for producing and/or tracking the shear wave, for measuring changes in position or velocity within the anatomical structure and compressive displacement difference (e.g., strain) of the tissue, and/or for treatment and other applications. For example, the probe 126 may deliver low energy pulses during imaging and tracking, deliver medium and high energy pulses to produce shear waves, and deliver high energy pulses during treatment.

The ultrasonic transducer converts a received echo signal into an electrical signal that can be received by a receiver. The receiver may include one or more amplifiers, analog/digital converters (ADCs), and the like. The receiver may be configured to amplify the received echo signal after appropriate gain compensation, and convert these analog signals received from each transducer element into a digitized signal that is temporally uniformly sampled. The digitized signals representing the received echoes are temporarily stored in the memory 106. The digitized signals correspond to backscattered waves received by each transducer element at different times. After being digitized, the signal may still retain the amplitude, frequency, and phase information of the backscattered wave.

Optionally, the controller circuit 102 may retrieve a digitized signal stored in the memory 106 for use in a beamformer processor. For example, the controller circuit 102 may convert the digitized signal into a baseband signal or compress the digitized signal.

In some embodiments, the controller circuit 102 may further include a beamforming processor. The beamformer processor may include one or more processors. If desired, the beamformer processor may include a central processing unit (CPU), one or more microprocessors, or any other electronic assembly capable of processing inputted data according to specific logic instructions. Additionally or alternatively, the beamformer processor may execute instructions stored on a tangible and non-transitory computer-readable medium (e.g., the memory 106) to perform beamforming computation using any suitable beamforming method, such as adaptive beamforming, synthetic emission focusing, aberration correction, synthetic aperture, clutter suppression, and/or adaptive noise control, etc.

In some embodiments, the controller circuit 102 may further include a radio frequency (RF) processor. The beamformer processor performs beamforming on the digitized signal of the transducer elements, and outputs an RF signal. The RF signal is then provided to an RF processor for processing the RF signal. The RF processor may include one or more processors. If desired, the RF processor may include a central processing unit (CPU), one or more microprocessors, or any other electronic assembly capable of processing inputted data according to specific logic instructions. Additionally or alternatively, the RF processor may execute instructions stored on a tangible and non-transitory computer-readable medium (e.g., the memory 106). If desired, the RF processor may be integrated with and/or be part of the controller circuit 102. For example, operations described as being performed by the RF processor may be configured to be performed by the controller circuit 102.

The RF processor may generate, for a plurality of scanning planes or different scanning modes, different ultrasonic image data types and/or modes, e.g., B-mode, color Doppler (e.g., color blood flow, velocity/power/variance), tissue Doppler (velocity), and Doppler energy, on the basis of a predetermined setting of a first model. For example, the RF processor may generate tissue Doppler data for multiple scanning planes. The RF processor acquires information (e.g., I/Q, B-mode, color Doppler, tissue Doppler, and Doppler energy information) related to multiple data pieces, and stores data information in the memory 106. The data information may include time stamp and orientation/rotation information.

Optionally, the RF processor may include a composite demodulator (not shown) for demodulating an RF signal to generate an IQ data pair representing an echo signal. The RF or IQ signal data may then be provided directly to the memory 106 so as to be stored (e.g., stored temporarily). As desired, output of the beamformer processor may be delivered directly to the controller circuit 102.

The controller circuit 102 may be configured to process acquired ultrasonic data (e.g., RF signal data or an IQ data pair), and prepare and/or generate an ultrasonic image data frame representing the anatomical structure of interest so as to display the same on the display device 138. The acquired ultrasonic data may be processed by the controller circuit 102 in real time when an echo signal is received in a scanning or treatment process of ultrasonic examination. Additionally or alternatively, the ultrasonic data may be temporarily stored in the memory 106 in a scanning process, and processed in a less real-time manner in live or offline operations.

The memory 106 may be used to store processed frames of acquired ultrasonic data that are not scheduled to be immediately displayed, or may be used to store post-processed images (e.g., shear wave images and strain images), firmware or software corresponding to, for example, a graphical user interface, one or more default image display settings, programmed instructions, and the like. The memory 106 may store a medical image, such as a 3D ultrasonic image data set of ultrasonic data, wherein such a 3D ultrasonic image data set is accessed to present 2D and 3D images. For example, a 3D ultrasonic image data set may be mapped to the corresponding memory 106 and one or more reference planes. Processing of ultrasonic data that includes the ultrasonic image data set may be based in part on user input, e.g., a user selection received at the user interface 142.

In some embodiments, the ultrasonic imaging system described above may be configured to be used for real-time imaging in an interventional operation. For example, the ultrasonic imaging system may be used to image the prostate to assist a physician in determining the position of a lesion. In the prior art, a physician needs to perform adjustment and manual determination according to a real-time imaging result, so that a lot of time and efforts are consumed, and it is difficult to ensure the accuracy. At least in view of this, improvements to the ultrasonic imaging method are made in embodiments of the present application below. An exemplary description is provided in some embodiments below by using ultrasonic imaging methods of the prostate, but it can be understood that the present application is not limited thereto.

Referring to FIG. 2, there shows a schematic diagram of an ultrasonic imaging method 200 according to some embodiments of the present application. The method 200 can be implemented by the ultrasonic imaging system disclosed in any embodiment herein.

In step 201, an ultrasonic echo signal from tissue to be imaged is received a plurality of times during movement of a first ultrasonic transducer. The process may be implemented by a processor, e.g., the processor in the controller circuit 102 in FIG. 1. The first ultrasonic transducer may likewise be as described in any embodiment of the present application.

In some embodiments, the first ultrasonic transducer may be moved manually. For example, in a prostate operation, a physician may manually operate a probe to advance the first ultrasonic transducer in the rectum of a person to be imaged, so as to receive an ultrasonic echo signal from the tissue to be imaged (e.g., the prostate) a plurality of times. In some other embodiments, the first ultrasonic transducer may be moved automatically by means of a driving device, e.g., the driving device 108 described above in the present application. It can be understood that an ultrasonic transducer may transmit and receive ultrasonic signals continuously within a certain time, and a physician may also perform adjustment.

In step 202, a first ultrasonic image set is generated on the basis of the ultrasonic echo signals, the ultrasonic image set including a plurality of ultrasonic images. The process may likewise be implemented by the processor in the controller circuit 102 in FIG. 1. A specific imaging method may be as described in any of the embodiments described above, and will not be further described herein. The first ultrasonic transducer continually images the tissue to be imaged while moving, so that a plurality of ultrasonic images regarding the tissue to be imaged can be acquired, thereby constituting the ultrasonic image set described above. The first ultrasonic transducer is being moved during imaging, so that the plurality of ultrasonic images correspond to different positions on the tissue to be imaged. Therefore, in each ultrasonic image, the position and size of the tissue to be imaged and the position and size of a structure of interest (e.g., a lesion) in the tissue to be imaged are also different. The plurality of ultrasonic images in the first ultrasonic image set can provide three-dimensional information of the tissue to be imaged and the structure of interest.

In step 203, outer contours of a structure of interest are identified in the plurality of ultrasonic images. The step may be implemented by the processor. A specific identification method may be any method in the art. In one embodiment, identification may be performed by means of an image analysis algorithm. For example, the structure of interest may be identified via anatomical features (a boundary, thickness, pixel value change, etc.) in the ultrasonic image. In another embodiment, identification may be performed by means of artificial intelligence, e.g., a deep learning algorithm, a convolutional neural network algorithm, a decision tree learning algorithm, etc. The exemplary description is provided above, and will not be repeated herein. In some embodiments, the structure of interest may be a lesion, e.g., a tumor. In some other embodiments, the structure of interest may also be a normal tissue in a particular position in the tissue to be imaged. Examples are not exhaustively enumerated.

In step 204, the outer contours of the structure of interest in the plurality of ultrasonic images are overlapped to acquire a reconstructed image. The step may be implemented by the processor. Each of the plurality of ultrasonic images in the ultrasonic image set includes two-dimensional contours of the tissue to be imaged and/or the structure of interest in a sectional direction thereof. Different ultrasonic images represent two-dimensional contours in different thickness or depth direction. By overlapping the outer contours of the structure of interest in the plurality of ultrasonic images, the entire outer contour of the structure of interest projected in the depth direction is acquired as a reconstructed ultrasonic image.

In such configurations, it is not necessary for a physician to manually determine the contour of the structure of interest in each of the plurality of ultrasonic images to estimate the size and contour of the entire structure of interest. The outer contour of the structure of interest in the reconstructed image can represent a complete contour projected in the depth direction. By observing the reconstructed image, a physician can quickly, accurately determine the size of the structure of interest.

Figure 3:
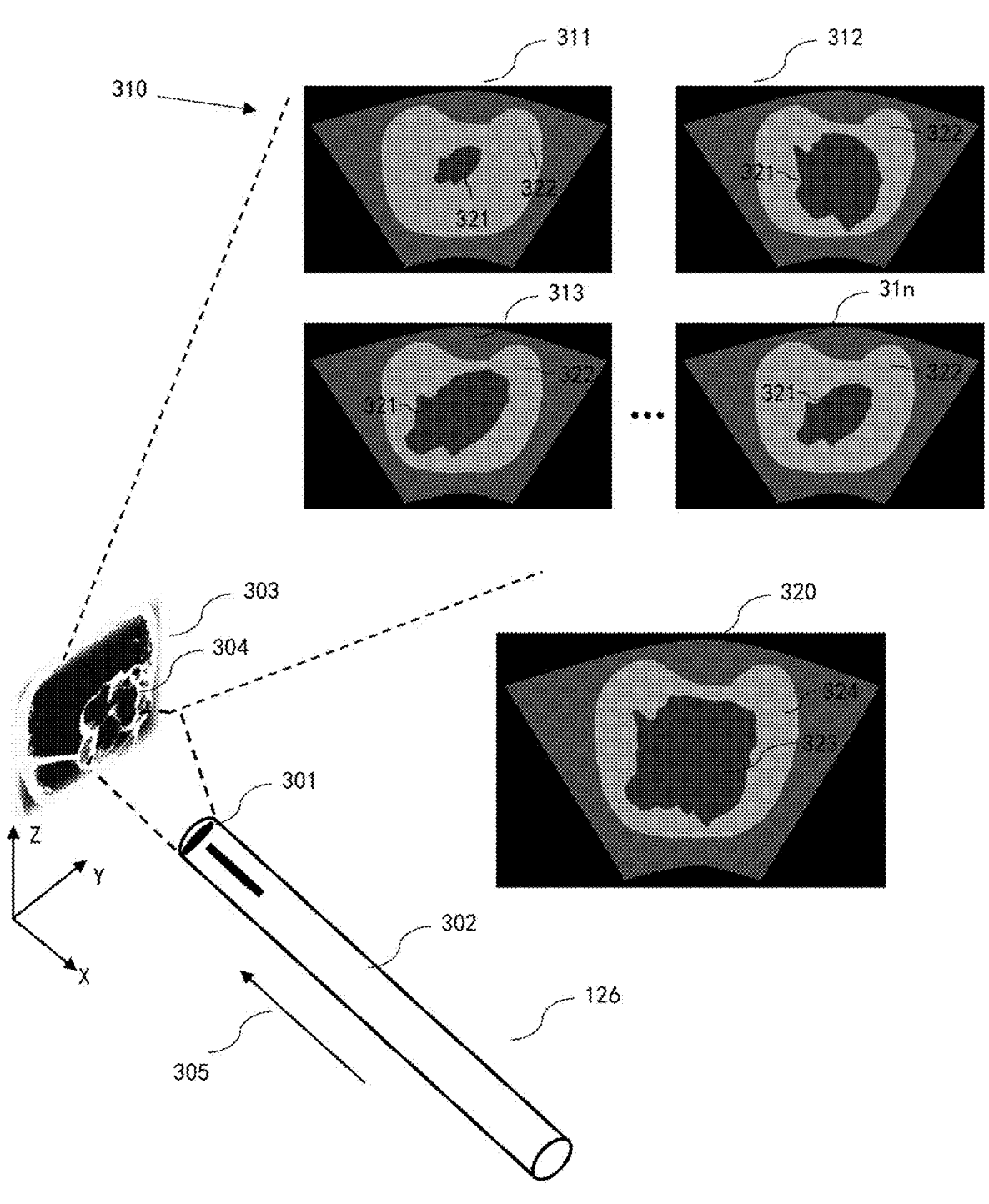
FIG. 3 is a schematic diagram of overlapping outer contours of a structure of interest in a plurality of ultrasonic images according to some embodiments of the present application.

The process of reconstruction described above will be described in further detail below by means of drawings. Referring to FIG. 3, there show a schematic diagram of overlapping outer contours of a structure of interest in a plurality of ultrasonic images according to some embodiments of the present application.

As shown in FIG. 3, the probe 126 includes a first ultrasonic transducer 301. In some embodiments, the first ultrasonic transducer 301 is provided at an end of the probe 126. Specifically, the probe 126 includes a stem portion 302, and the first ultrasonic transducer 301 is provided at an end of the stem portion 302 and extends in a peripheral direction of the stem portion 302 to form a curved shape. The first ultrasonic transducer 301 provided at the end of the probe 126 can ensure that once the probe 106 enters the body (e.g., the rectum), the first transducer 301 can transmit and acquire ultrasonic signals to perform imaging. As the probe 126 is moved, the first ultrasonic transducer 301 continually images tissue 303 to be imaged (e.g., the prostate) in a depth direction, and generates an ultrasonic image set 310 including a plurality of two-dimensional ultrasonic images 311-31$n$.

In the ultrasonic image set 310, each ultrasonic image represents an imaging result of the first ultrasonic transducer 301 regarding the tissue 303 to be imaged in a certain depth direction (an X-axis direction). A structure 304 of interest (e.g., a lesion) in the tissue 303 to be imaged has different contours in different depth directions 305, so that a structure 321 of interest in each ultrasonic image in the ultrasonic image set 310 has different topology. In this case, overlapping the outer contours of the structure 321 of interest in the plurality of ultrasonic images 311-31$n$ can acquire a reconstructed image 320. The reconstructed image 320 includes a reconstructed outer contour of a structure 323 of interest. The reconstructed outer contour of the structure 323 of interest can be understood as an outer contour projection in a depth direction, and can fully reflect the size of the entire structure of interest in the depth direction, thereby making it easier for the physician to make a decision fast and accurately.

In some embodiments, each ultrasonic image in the ultrasonic image set 310 is essentially parallel to a first plane, i.e., a Y-Z plane direction shown in FIG. 3. Such configurations can ensure that the outer contour of the structure 321 of interest in each ultrasonic image is aligned in the depth direction. Correspondingly, it can be ensured that the outer contour after the overlapping reflects accurately the outer contour of the entire structure of interest in a projection direction.

A plane where the ultrasonic image is located depends on a plane where echoes of an ultrasonic transducer are located. In order to ensure that each ultrasonic image is essentially parallel to the first plane, in some embodiments of the present application, the first ultrasonic transducer is moved generally in a straight-line direction 305 perpendicular to the first plane. The first ultrasonic transducer may be moved manually, or may be moved by means of the driving device recited in the embodiments described above, and details will not be described herein again. In such configurations, the first ultrasonic transducer 301 is advanced in the straight-line direction 305 (i.e., the depth direction, or the X-axis direction) perpendicular to the first plane, so that it is ensured that the ultrasonic images 311-31n in the ultrasonic image set 310 are parallel to each other, thereby facilitating image overlapping.

In some embodiments, an outer contour of the tissue to be imaged may also be reconstructed. With continued reference to FIG. 3, in the ultrasonic image set, each ultrasonic image further includes tissue 322 to be imaged. In some embodiments, the outer contours of the tissue 322 to be imaged in the plurality of ultrasonic images can be identified, so as to overlap the outer contours of the tissue 322 to be imaged in the plurality of ultrasonic images, thereby ultimately acquiring a reconstructed outer contour of the tissue 324 to be imaged. An identification method may be as described herein in any of the embodiments described above. For example, the identification can be performed by using the same method as the identification of the structure of interest. Further, a method for overlapping the outer contours of the tissue 322 to be imaged may also be as described herein in any of the embodiments described above, and will not be described herein again.

Such configurations make it easier for the physician to more fully learn the size of the outer contour of the tissue to be imaged in a depth projection direction during operation, thereby enabling direct comparison with the size of the structure of interest.

Figure 4:
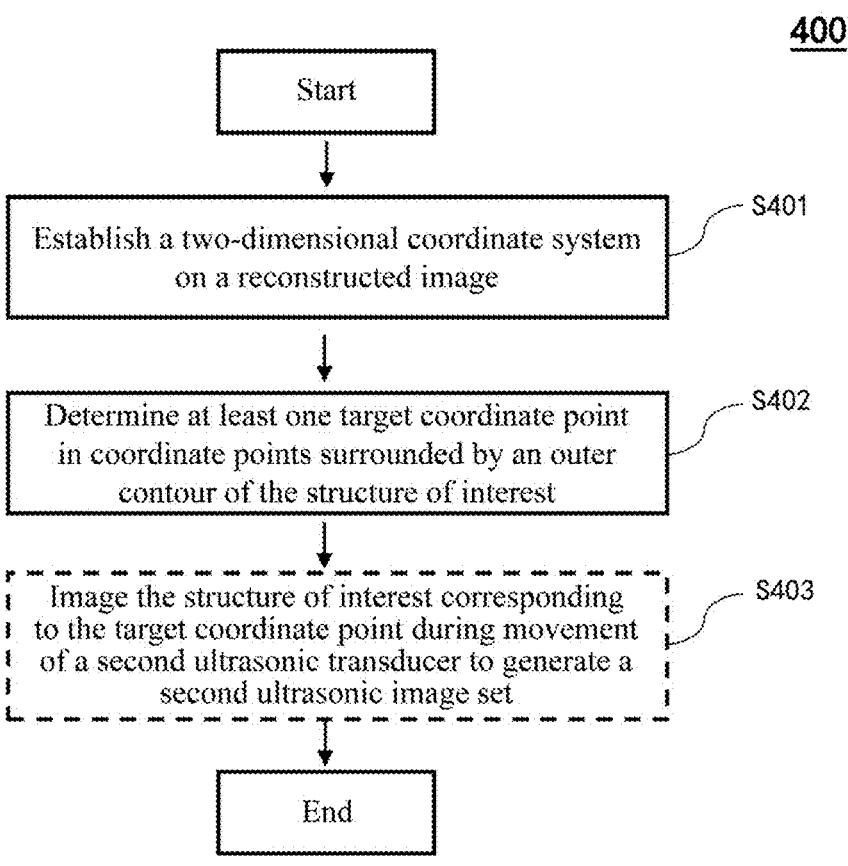
FIG. 4 is a schematic diagram of an ultrasonic imaging method according to some other embodiments of the present application.

After the outer contours of the tissue to be imaged and/or the structure of interest are imaged, the physician may perform a next operation with reference to the reconstructed image, for example, implementing an interventional operation. Considering that implementation of an interventional operation requires accurate positioning of a structure of interest, such as a lesion, improvements are provided in some embodiments of the present invention. Referring to FIG. 4, there shows an ultrasonic imaging method 400 in some other embodiments of the present application.

In step 401, a two-dimensional coordinate system is established on a reconstructed image. The two-dimensional coordinate system includes a plurality of coordinate points. The step may also be performed by a processor. Specifically, a two-dimensional coordinate system including an abscissa and an ordinate may be established on the reconstructed image. The coordinate system may include the abscissa, ordinate, and a plurality of coordinate points in the two-dimensional coordinate system. In addition, as can be seen from the above description of the embodiments, the reconstructed image includes reconstructed outer contours of a structure of interest and/or tissue to be imaged. In this case, all coordinate points surrounded by the reconstructed outer contour of the structure of interest can be observed on the reconstructed image. In embodiments of the present application, the outer contour of the structure of interest is reconstructed, so that correspondingly, all the coordinate points surrounded thereby can accurately and fully reflect the range of the structure of interest on the reconstructed image.

Figure 5:
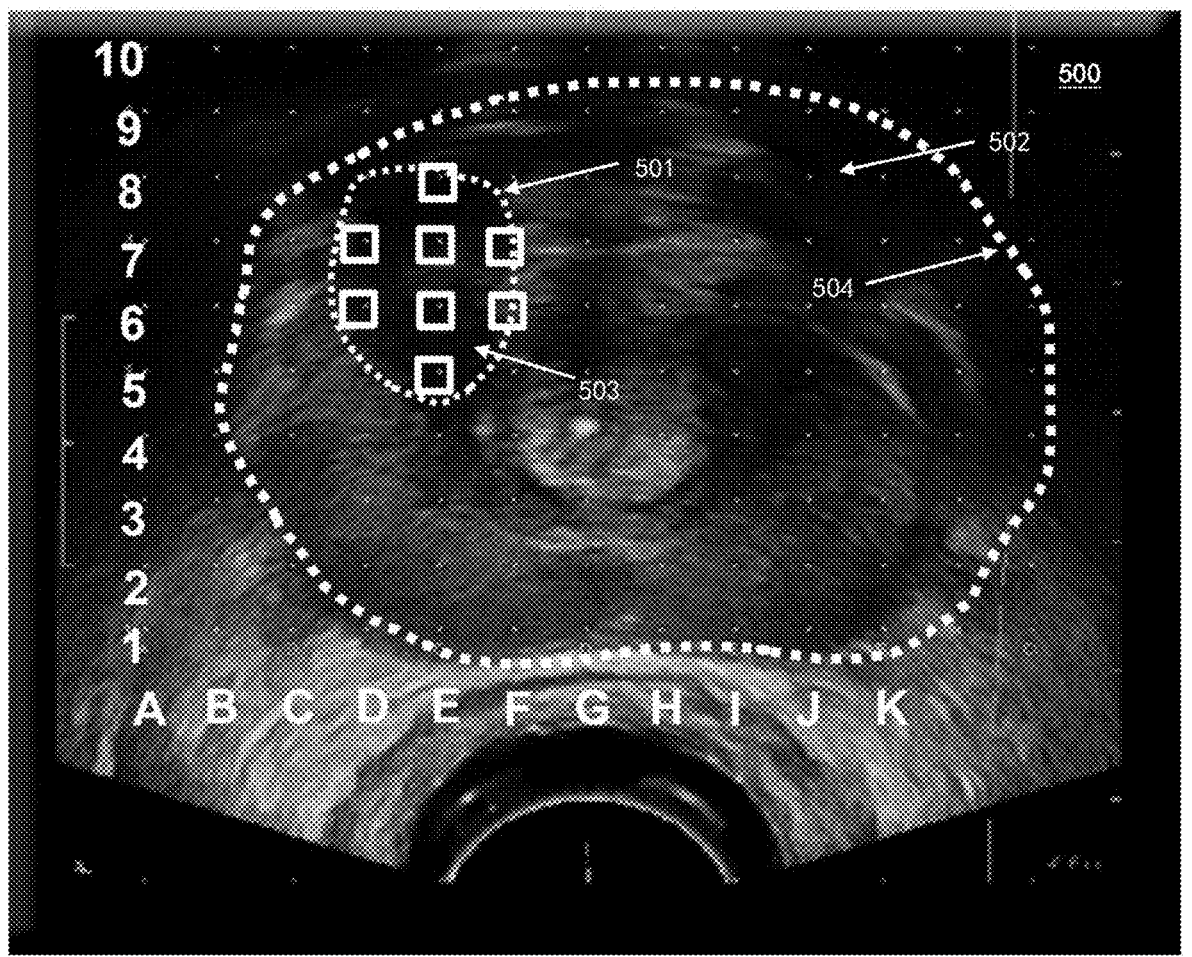
FIG. 5 is a schematic diagram of a reconstructed image including a two-dimensional coordinate system according to some embodiments of the present application.

Establishment of a two-dimensional coordinate system will be described in further detail with reference to FIG. 5. FIG. 5 shows a reconstructed image 500 including a two-dimensional coordinate system in some embodiments of the present application. As shown in FIG. 5, the reconstructed ultrasonic image 500 includes a reconstructed structure 501 of interest and tissue 502 to be imaged. In addition, the ultrasonic image 500 further includes a two-dimensional coordinate system. The two-dimensional coordinate system includes abscissas represented by the letters A to K and ordinates represented by the numbers 1 to 10. In addition, in the two-dimensional coordinate system, there are also a plurality of coordinate points (represented by dots). The coordinate points are provided so that when a physician selects a certain specific position, the physician can easily determine specific coordinates of the position, thereby facilitating operation. Further, as can be seen from FIG. 5, an outer contour of the structure of interest surrounds coordinate points D6, D7, E5, E6, E7, E8, F6, and F7 (represented by square boxes). In this way, the outer contour 401 of the structure of interest can be accurately and completely positioned.

Continue to refer to FIG. 4. In step 402, at least one target coordinate point in coordinate points surrounded by the outer contour of the structure of interest is determined. The target coordinate point may be understood as a coordinate point that a user is interested in. In some cases, the number of target coordinate points may be one. In some other cases, the number of target coordinate points may be multiple, or the target coordinate points are all coordinate points surrounded by the outer contour of the structure of interest.

The target coordinate point may be selected by means of a variety of methods. In one embodiment, the target coordinate point may be selected by a user manually, for example, by a physician by means of a trackball, a mouse, a touch screen, a keyboard, or the like, and may be selected according to actual requirements. For example, when a physician performs a biopsy, a coordinate point close to a middle position may be selected from the coordinate points surrounded by the outer contour of the structure of interest, or a plurality of coordinate points may be selected discretely to achieve better coverage. Alternatively, during drug treatment, a physician may reasonably select a coordinate point according to an effective range of a drug that needs to be placed in a lesion. In another embodiment, the target coordinate point may be automatically selected by a processor. For example, the processor of the ultrasonic imaging system may automatically screen the coordinate points surrounded by the outer contour of the structure of interest to acquire the target coordinate point. For example, the processor may select a suitable number of target points according to the size and shape of the outer contour of the reconstructed structure of interest.

The above configurations can reduce cumbersome work procedures resulting from manual operation, and can accurately satisfy different requirements of physicians. For example, for the purpose of assisting a biopsy, the processor may be automatically configured to select several coordinate points distributed evenly inside the outer contour so as to effectively improve the accuracy of sampling. Alternatively, for the purpose of assisting treatment, the processor may automatically exclude, according to an effective range of a drug, target points that would be affected repeatedly, thereby ensuring the effectiveness of the treatment and minimization of a drug dosage. The method described above avoids the problem of cumbersome and time-consuming manual operation, thereby improving working efficiency.

Figure 6:
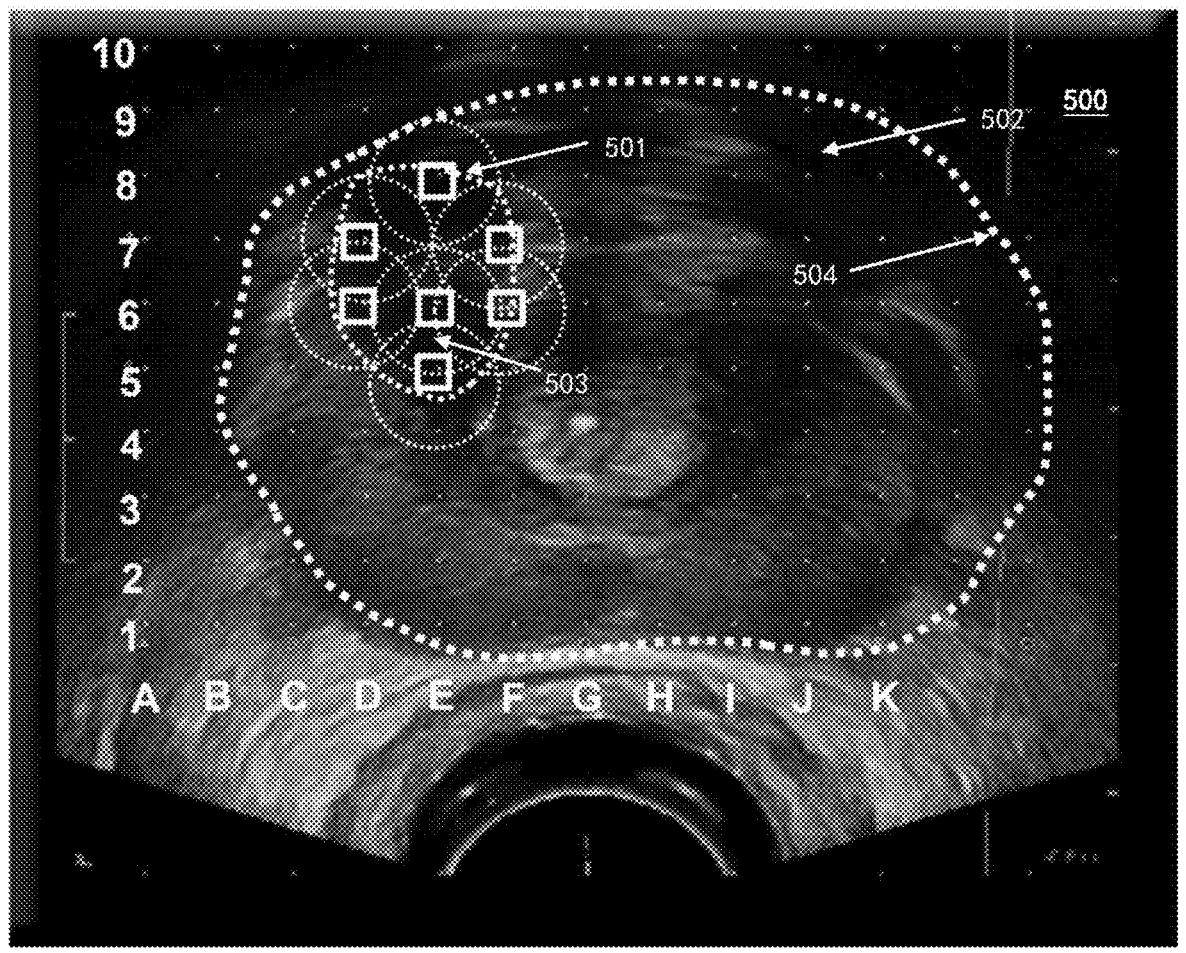
FIG. 6 is a schematic diagram of determining at least one target coordinate point in coordinate points surrounded by an outer contour of a structure of interest according to some embodiments of the present application.

Selection of the target coordinate point is further described with reference to FIG. 6. FIG. 6 shows a schematic diagram of determining at least one target coordinate point in coordinate points surrounded by an outer contour of a structure of interest according to some embodiments of the present application. Similar to that in the embodiment corresponding to FIG. 5, a reconstructed ultrasonic image 500 in FIG. 6 includes a reconstructed structure 501 of interest, tissue 502 to be imaged, and a two-dimensional coordinate system. As an example, an outer contour of the structure of interest in FIG. 6 surrounds coordinate points D6, D7, E5, E6, E7, E8, F6, and F7. When a physician needs to perform drug treatment on the structure of interest, such as a tumor, the processor may determine target coordinate points according to an effective range (represented by dashed circles surrounding coordinate points in FIG. 6) of a drug. As shown in FIG. 6, the processor automatically determines that the position of the coordinate E7 is well covered by the effective range of the drug in other coordinate points. In this case, the processor determines that no drug needs to be additionally applied to the coordinate point E7, and therefore excludes the coordinate point E7 from target coordinate points. That is, D6, D7, E5, E6, E8, F6, and F7 are selected as target coordinate points. Such configurations can make it easier for the physician to perform determination rapidly, and can effectively reduce the drug dosage. It should be noted that the coordinate points and the selection of target coordinate points shown in FIG. 6 are merely exemplary descriptions, and do not uniquely define the present application. The selection of target coordinate points may also be as described herein in any of the embodiments described above, and examples are not exhaustively enumerated. Moreover, determination of the target coordinate point being used to assist drug application is one of embodiments of the present application, and may also be used for other purposes, for example, biopsies or other arbitrary application scenarios.

The method described in the embodiments described above can completely and fully image outer contours of a structure of interest and/or tissue to be imaged in the depth projection direction. It is recognized by the applicant that in some use scenarios, a user may further need information in a depth direction. That is, the depth of a structure of interest, such as a tumor, relative to the body surface or the surface of a specific tissue to be imaged. At least in view of the objective described above, improvements are provided in some embodiments of the present application. Detailed description is provided below.

Refer back to FIG. 4. In step 403, the structure of interest corresponding to the target coordinate point is imaged during movement of a second ultrasonic transducer to generate a second ultrasonic image set. Each ultrasonic image in the second ultrasonic image set is perpendicular to the first plane and passes through at least one target coordinate point. As described above in the present application, ultrasonic echo signals acquired by the first ultrasonic transducer are processed to generate the first ultrasonic image set consisting of a series of parallel ultrasonic images. The ultrasonic images in the first ultrasonic image set are parallel to the first plane. The ultrasonic images parallel to the first plane provide information on the cross section of the structure of interest and the tissue to be imaged. In step 403, ultrasonic images in the second ultrasonic image set are acquired by the second ultrasonic transducer in a direction perpendicular to the first plane. With respect to the ultrasonic image, the ultrasonic images of the second ultrasonic image set are perpendicular to the ultrasonic images of the first ultrasonic image set. That is, the ultrasonic images in the second ultrasonic image set can reflect information in the depth direction. Further, the ultrasonic images in the second ultrasonic image set further pass through at least one target coordinate point.

Such configurations can ensure that the target coordinate point has not only a cross section image (from the first ultrasonic image set) but also a section image (from the second ultrasonic image set) in the depth direction, so that more comprehensive information can be provided to a physician.

Figure 7:
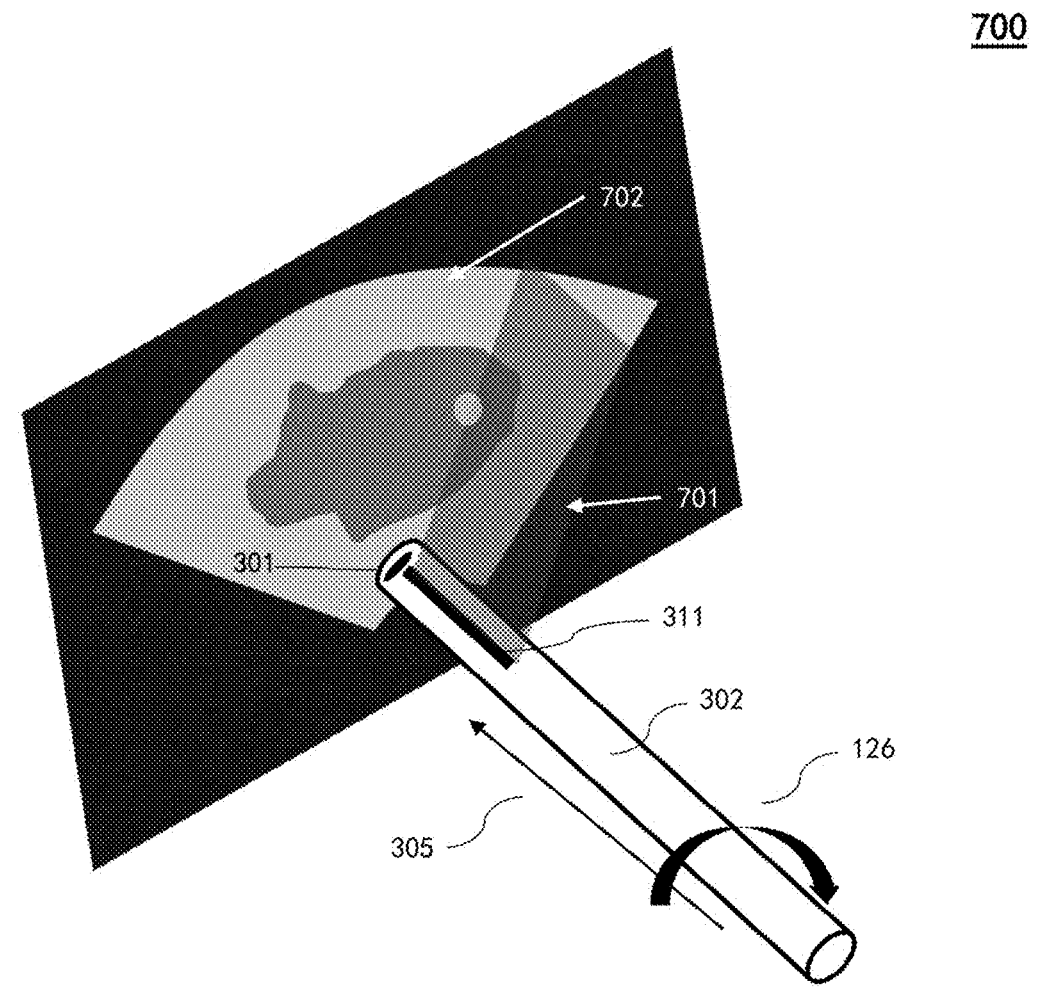
FIG. 7 is a schematic diagram of performing imaging by using a second ultrasonic transducer according to some embodiments of the present application.

An exemplary description of acquiring images by using the second ultrasonic transducer is provided below. Referring to FIG. 7, there shows a schematic diagram of performing imaging by using a second ultrasonic transducer 311 according to some embodiments of the present application. In some embodiments, the second ultrasonic transducer 311 shown in FIG. 7 and the first ultrasonic transducer 301 shown in FIG. 3 May be located on the same probe 126. The first ultrasonic transducer 301 is provided at an end of the stem portion 302 of the probe 126, and is configured to extend in a peripheral direction of the stem portion to form a curved shape. The second ultrasonic transducer 311 extends in a lengthwise direction of the stem portion 302, and is essentially perpendicular to a plane where the curved shape of the first ultrasonic transducer 301 is located. Such configurations can ensure that a plane where an ultrasonic echo signal 701 acquired by the second ultrasonic transducer 311 is located is essentially perpendicular to a plane where an ultrasonic echo signal acquired by the first ultrasonic transducer is located. Correspondingly, it can be ensured that the plane where the ultrasonic image in the second ultrasonic image set is located is essentially perpendicular to the plane where the ultrasonic image in the first ultrasonic image set is located. It should be understood that being essentially perpendicular means that a certain deviation is allowed. Moreover, although FIG. 3 and FIG. 7 show that the first ultrasonic transducer 301 and the second ultrasonic transducer 302 are integrated in the same probe 126, the first ultrasonic transducer and the second ultrasonic transducer may respectively belong to different probes in some other embodiments.

The second ultrasonic transducer 311 may be moved in a variety of manners. In one example, the second ultrasonic transducer may be moved by means of the driving device 108 described above. Specifically, the processor may send a signal to the driving device 108 to control the driving device 108 to drive the probe 126 to move so as to drive the second ultrasonic transducer 311 to move, thereby facilitating fully automated image acquisition. In another example, the second ultrasonic transducer 311 may also be moved manually.

Further, the second ultrasonic transducer 311 may be configured to be rotated generally about a straight-line direction 305 perpendicular to the first plane. As described above, the probe may be configured to have a stem portion 302, and the second ultrasonic transducer 311 extends in the lengthwise direction of the stem portion 302. Correspondingly, rotation of the probe can achieve rotation of the second ultrasonic transducer 311 in an intended direction. As the second ultrasonic transducer 311 rotates, ultrasonic images of different positions are acquired. It can be understood that controlling different angles of rotation can control the second ultrasonic transducer 311 to acquire ultrasonic images of different positions.

In some cases, selection of the angle of rotation can be determined according to the target coordinate point recited in the embodiments described above. For example, a current deflection angle of the second ultrasonic transducer 311 may be determined first, and then an included angle between a connecting line from the target coordinate point to the probe and the current deflection angle is calculated, thereby determining the angle of rotation required for the second ultrasonic transducer. When a plurality of target coordinate points are present, the process described above may be repeated until image acquisition is completed. The process described above may be automatically accomplished by the processor by controlling the driving device. Such configurations can ensure that the probe is rotated as less as possible, and thus a path of rotation is planned, thereby reducing unnecessary rotation operations. In an aspect, workload on an operator is reduced, and in another aspect, a patient has less pains caused by movement of the probe in the body.

In some other cases, the selection of the angle of rotation may be preset. For example, the rotation is performed clockwise or counterclockwise in a fixed manner. The operations described above generate a large number of ultrasonic images constituting the second ultrasonic image set. These images may further be used to be associated with the target coordinate points. For example, one ultrasonic image may be selected as a reference image, and then an included angle between a connecting line from each target coordinate point to the probe and the reference image is respectively determined. In turn, a corresponding ultrasonic image in the second ultrasonic image set is searched for according to the calculated included angle, and is considered an ultrasonic image passing through the target coordinate point. In addition, under the teaching of the present disclosure, other calculation methods are also allowed. Examples are not exhaustively enumerated herein.

By means of the embodiments described above, ultrasonic images in the depth direction can be acquired by using the second ultrasonic transducer, and these ultrasonic images can further be associated with target coordinate points, thereby providing more comprehensive imaging information to a physician.

Figure 8:
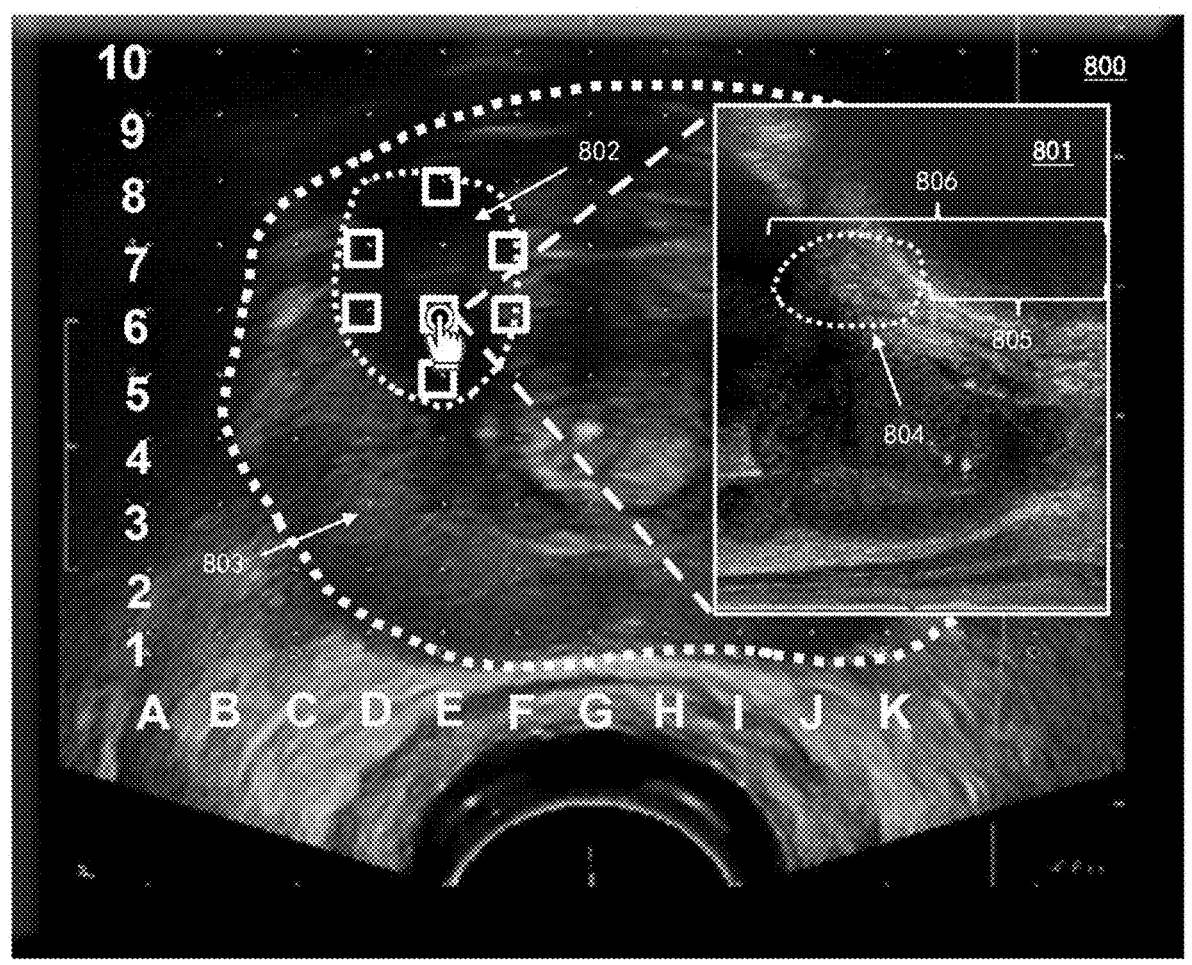
FIG. 8 is a schematic diagram of displaying an ultrasonic image according to some embodiments of the present application.

A method for presenting imaging information is described in further detail below by means of examples. Referring to FIG. 8, there shows a schematic diagram of displaying an ultrasonic image according to some embodiments of the present application. In this embodiment, the reconstructed image 800 is displayed, and in response to that a target coordinate point (e.g., E6) is selected, an ultrasonic image 801 passing through the selected target coordinate point in the second ultrasonic image set is simultaneously displayed. A method for reconstructing the reconstructed image 800 and a method for determining the target coordinate point may be as recited herein in any of the embodiments described above. Moreover, the target coordinate point E6 may be selected on the basis of an operation performed on an input device by a user. For example, the user may select any one of several target coordinate points by operating a trackball, a touch pad, a keyboard, or any other type of user input to click or move a cursor on the display device, or the like. Upon receiving a signal indicating that a target coordinate point is selected, the processor automatically displays the ultrasonic image 801 passing through the selected target coordinate point in the second ultrasonic image set. In this case, the reconstructed image 800 and the ultrasonic image 801 are simultaneously displayed on the display device, thereby making it easier for a user to view the same. The reconstructed image 800 can provide a physician with dimension information of a structure 802 of interest and tissue 803 to be imaged in the cross section direction, and meanwhile, the ultrasonic image 801 can provide the physician with depth information at the selected target point E6. In some other embodiments, display of the ultrasonic image 801 may also be automatically canceled in response to canceling of selection of the target coordinate point. For example, after the cursor is moved away from the target coordinate point, the ultrasonic image 801 is accordingly no longer displayed.

The configurations described above can provide more comprehensive image information to a physician. In addition, the ultrasonic image providing the depth information is presented on the basis of selection of the target coordinate point, thereby effectively avoiding the case where information is presented aimlessly because too many ultrasonic images are displayed simultaneously.

It is further recognized by the inventor that more useful information can also be provided in addition to that the ultrasonic images described above are provided. In some embodiments, depth information of the structure of interest may also be displayed on the ultrasonic image passing through the selected target point. The depth information may be presented in a variety of manners. For example, the outer contour of the structure of interest in the current ultrasonic image 801 may be included. Alternatively, a shortest distance 805 between a horizontal line passing through a current coordinate point (e.g., E6) and a puncture point or a skin surface may be included. Alternatively, a longest distance 806 between a horizontal line passing through a current coordinate point (e.g., E6) and a puncture point or a skin surface may be included. The height of the current coordinate point (or the distance in the Y-axis direction) may be calculated in a variety of manners. In one example, determination may be performed by means of calculation of the length of a perpendicular line (not shown) between the stem portion of the probe 106 and the target point. In another example, calculation may be performed in another manner. Examples are not enumerated herein. Moreover, in some examples, the depth information described above may include any one or more of the examples described above. The information described above is provided, so that a physician observing an ultrasonic image passing through a selected target point can more comprehensively learn the size and depth of a structure of interest in the position, thereby facilitating decision-making regarding sampling, a drug dosage, or the like.

It will be appreciated that the above merely schematically illustrates the embodiments of the present application, but the present application is not limited thereto. For example, the order of execution between operations may be appropriately adjusted. In addition, some other operations may be added or some operations may be omitted. A person skilled in the art could make appropriate variations according to the above disclosure, rather than being limited by the above descriptions.

Some embodiments of the present application further provide an ultrasonic imaging system, which may be as shown in FIG. 1 or any other ultrasonic imaging system. The system includes: a probe, including a first ultrasonic transducer; a processor, configured to perform the method according to any of the embodiments of the present application described above; and a display device, configured to receive a signal from the processor and perform a display operation.

Some embodiments of the present application further provide a non-transitory computer-readable medium, having a computer program stored therein, the computer program having at least one code segment, and the at least one code segment being executable by a machine so as to enable the machine to perform the steps of the method in any of the embodiments described above.

Correspondingly, the present disclosure may be implemented as hardware, software, or a combination of hardware and software. The present disclosure may be implemented in at least one computer system by using a centralized means or in a distributed means, different elements in the distributed means being distributed on a number of interconnected computer systems. Any type of computer system or other device suitable for implementing the methods described herein is considered to be appropriate.

The various embodiments may also be embedded in a computer program product, which includes all features capable of implementing the methods described herein, and the computer program product is capable of executing these methods when loaded into a computer system. The computer program in the present context means any expression in any language, code, or symbol of an instruction set intended to enable a system having information processing capabilities to execute a specific function directly or after any one or two among a) conversion into another language, code, or symbol; and b) duplication as a different material.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. An ultrasonic imaging system, comprising:
a probe, comprising a stem portion and a first ultrasonic transducer provided at an end of the stem portion and extending in a peripheral direction of the stem portion to form a curved shape;
a second ultrasonic transducer extending in a lengthwise direction of the stem portion and oriented substantially perpendicular to a plane where the curved shape of the first ultrasonic transducer; is located;
a memory storing instructions;
a processor configured to execute the instructions to:
during movement of the first ultrasonic transducer, receive, over a period of time, an ultrasonic echo signal from tissue to be imaged;
generate a first ultrasonic image set based on the received ultrasonic echo signal, the first ultrasonic image set comprising a plurality of ultrasonic images;
identify outer contours of a structure of interest in the plurality of ultrasonic images; and
overlap the outer contours of the structure of interest in the plurality of ultrasonic images to acquire a reconstructed image; and
a display device, configured to receive a signal from the processor and perform display, further comprising:
a driving device, connected to the probe and configured to drive the probe to move.

2. An ultrasonic imaging method, comprising:
during movement of a first ultrasonic transducer array, receiving, over a period of time, an ultrasonic echo signal from tissue to be imaged, wherein the first ultrasonic transducer array is rotated generally about a straight-line direction parallel to a first plane;
generating a first ultrasonic image set comprising a plurality of ultrasonic images that are parallel to the first plane based on the received ultrasonic echo signal;
identifying outer contours of a structure of interest in the plurality of ultrasonic images;

acquiring a reconstructed image based on the outer contours of the structure of interest in the plurality of ultrasonic images;
establishing a two-dimensional coordinate system on the reconstructed image and determining at least one target coordinate point surrounded by the outer contour; and
performing imaging during movement of a second ultrasonic transducer to generate a second ultrasonic image set by controlling a second ultrasound array to rotate generally about a straight-line direction perpendicular to the first plane to image the at least one target coordinate point surrounded by the outer contour.

3. The method according to claim 2, further comprising:
identifying outer contours of the tissue in the plurality of ultrasonic images; and
overlapping the outer contours of the tissue in the plurality of ultrasonic images.

4. The method according to claim 3, wherein the first ultrasonic transducer is moved in a straight-line direction perpendicular to the first plane.

5. The method according to claim 3, further comprising:
displaying the reconstructed image; and
in response to a target coordinate point of the at least one target coordinate point being selected, simultaneously displaying the ultrasonic image in the second ultrasonic image set which passes through the selected target coordinate point.

6. The method according to claim 5, further comprising:
displaying, on the ultrasonic image passing through the selected target point, depth information of the structure of interest.

7. The method according to claim 3, wherein the second ultrasonic transducer is rotated generally about a straight-line direction perpendicular to the first plane.

8. A non-transitory computer-readable medium, having a computer program stored thereon, the computer program having at least one code segment, and the at least one code segment being executable by a machine to enable the machine to:
during movement of a first ultrasonic transducer array, receive, over a period of time, an ultrasonic echo signal from tissue to be imaged, wherein the first ultrasonic transducer array is rotated generally about a straight-line direction parallel to a first plane;
generate a first ultrasonic image set based on the received ultrasonic echo signal, the first ultrasonic image set comprising a plurality of ultrasonic images;
identify outer contours of a structure of interest in the plurality of ultrasonic images;
acquire a reconstructed image based on the outer contours of the structure of interest in the plurality of ultrasonic images;
in response to a user selection of a coordinate point on the reconstructed image, display a corresponding ultrasonic image from a second image set that intersects the selected point and includes depth information of the structure of interest; and
perform imaging during movement of a second ultrasonic transducer to generate a second ultrasonic image set by controlling a second ultrasound array to rotate generally about a straight-line direction perpendicular to the first plane to image the at least one target coordinate point surrounded by the outer contour.

9. The non-transitory computer-readable medium according to claim 8, wherein each ultrasonic image in the first ultrasonic image set is parallel to a first plane.

10. The non-transitory computer-readable medium according to claim 8, wherein the at least one code segment is executable by the machine to enable the machine to:

identify outer contours of the tissue to be imaged in the plurality of ultrasonic images; and overlap the outer contours of the tissue to be imaged in the plurality of ultrasonic images.

11. The non-transitory computer-readable medium according to claim 9, wherein the first ultrasonic transducer is moved in a straight-line direction perpendicular to the first plane.

12. The non-transitory computer-readable medium according to claim 9, wherein the at least one code segment is executable by the machine to enable the machine to:

establish a two-dimensional coordinate system on the reconstructed image, the two-dimensional coordinate system comprising a plurality of coordinate points; and determine at least one target coordinate point in coordinate points surrounded by the outer contour of the structure of interest.

13. The non-transitory computer-readable medium according to claim 12, wherein any ultrasonic image in the second ultrasonic image set is perpendicular to the first plane and passes through at least one of the target coordinate points.

14. The non-transitory computer-readable medium according to claim 12, wherein the at least one code segment is executable by the machine to enable the machine to:

display the reconstructed image; and in response to a target coordinate point being selected, simultaneously display the ultrasonic image in the second ultrasonic image set which passes through the selected target coordinate point.

\* \* \* \* \*